United States Patent [19]
Lesher et al.

[11] 4,354,026
[45] Oct. 12, 1982

[54] 3-CHLORO-6-(PYRIDINYL)-PYRIDAZINES

[75] Inventors: George Y. Lesher, Schodack; William B. Dickinson, Albany, both of N.Y.

[73] Assignee: Sterling Drug Inc., New York, N.Y.

[21] Appl. No.: 238,229

[22] Filed: Feb. 26, 1981

Related U.S. Application Data

[60] Division of Ser. No. 173,004, Jul. 28, 1980, Pat. No. 4,304,775, which is a continuation-in-part of Ser. No. 103,192, Dec. 13, 1979, abandoned.

[51] Int. Cl.³ .......................................... C07D 401/04
[52] U.S. Cl. .................................................. 544/238
[58] Field of Search ........................................ 544/238

[56] References Cited
PUBLICATIONS

Anderson et al., Chem. Abs. 77, 114418n, (1971).
Petric, Chem. Abs. 84, 74205b, (1975).
Rosseels et al., Chem. Abs. 64, 12474e, (1966).

Primary Examiner—Mark L. Berch
Attorney, Agent, or Firm—Robert K. Bair; B. Woodrow Wyatt

[57] ABSTRACT

3-Hydrazino-6-PY-pyridazine or pharmaceutically-acceptable acid-addition salt thereof is useful as a cardiotonic agent, where PY is 4- or 3-pyridinyl or 4- or 3-pyridinyl having one or two lower-alkyl substituents. 6-PY-3-pyridazinol is prepared by reacting 6-PY-3-pyridazinol with a chlorinating agent to produce 3-chloro-6-PY-pyridazine and reacting said 3-chloro compound with hydrazine to produce said 3-hydrazino compound. 3-Hydrazino-6-PY-pyridazine or pharmaceutically-acceptable acid-addition salt thereof is disclosed as the active component in cardiotonic compositions for increasing cardiac contractility and in the method for increasing cardiac contractility in a patient requiring such treatment. The novel intermediate 3-chloro-6-PY-pyridazine is prepared as noted above.

2 Claims, No Drawings

3-CHLORO-6-(PYRIDINYL)-PYRIDAZINES

CROSS-REFERENCE TO RELATED APPLICATIONS

This application is a division of copending Application Ser. No. 173,004, filed July 28, 1980 and now U.S. Pat. No. 4,304,775, issued Dec. 8, 1981, in turn a continuation-in-part of its copending Application Ser. No. 103,192, filed Dec. 13, 1979 and now abandoned.

The 6-PY-3-pyridazinols which are used as intermediates in the instantly claimed process are disclosed and claimed in the form of their tautomeric 6-PY-3(2H)-pyridazinones in copending application Ser. No. 144,576, filed Apr. 28, 1980 and now U.S. Pat. No. 4,304,777, issued Dec. 8, 1981, in turn a continuation-in-part of its copending application Ser. No. 71,065, filed Aug. 30, 1979 and now abandoned, where PY is defined hereinbelow.

BACKGROUND OF THE INVENTION (a) Field of the Invention

This invention relates to 3-hydrazino-6-PY-pyridazine, useful as cardiotonic agent, and to its preparation.

(b) Description of the Prior Art

Haginiwa et al. [Yakugaku Zasshi 98 (1), 67–71 (1978); Chem. Abstrs. 88, 170,096v (1978)] reacted 3(2H)-pyradazinone with pyridine 1-oxide and platinized Pd-C catalyst to produce 6-(2-pyridinyl)-3(2H)-pyridazinone.

The Yoshitomi Pharmaceutical Ind., Ltd. Japanese Patent Application Disclosure No. 19,987/79, published Feb. 15, 1979 and based on Application Ser. No. 85,192/77, filed July 15, 1977, discloses, inter alia, the preparation of 4,5-dihydro-6-(4-pyridinyl)-3(2H)-pyridazinone by refluxing for two hours an ethanolic solution of 3-(isonicotinoyl)propanoic acid [same as γ-oxo-γ-(4-pyridinyl)butyric acid] and hydrazine hydrate. 4,5-Dihydro-6-(4-pyridinyl)-3(2H)-pyridazinone and closely related 4,5-dihydro-6-(4- or 3- or 2-pyridinyl)-5-R-3(2H)-pyridazinones, where R is H or lower alkyl, are said (page 2 of English translation) to be "useful not only as medicines such as hypotensive and antithrombus agents because they have pharmacological actions such as hypotensive, blood platelet coagulation-inhibitory and membrane-stabilizing actions, but also as intermediates for the synthesis of such medicines".

SUMMARY OF THE INVENTION

In a composition of matter aspect, the invention resides in the compound, 3-hydrazino-6-PY-pyridazine or pharmaceutically-acceptable acid-addition salt thereof, useful as a cardiotonic agent, where PY is defined hereinbelow.

In a process aspect of the invention comprises reacting 6-PY-3-pyridazinol with a chlorinating agent to produce 3-chloro-6-PY-pyridazine and reacting the 3-chloro compound with hydrazine to produce 3-hydrazino-6-PY-pyridazine.

In another composition of matter aspect the invention resides in the compound 3-chloro-6-PY-pyridazine or pharmaceutically-acceptable salt thereof, useful as an intermediate in preparing the corresponding 3-hydrazino compound (supra).

A composition aspect of the invention relates to a cardiotonic composition for increasing cardiac contractility in a patient, said composition comprising a pharmaceutically-acceptable carrier and, as the active component thereof, the cardiotonic 3-hydrazino-6-PY-pyridazine or pharmaceutically-acceptable acid-addition salt thereof.

In a method aspect, the invention relates to a method for increasing cardiac contractility in a patient requiring such treatment which comprises administering to such patient an effective amount of the cardiotonic 3-hydrazino-6-PY-pyridazine or pharmaceutically-acceptable acid-addition salt thereof.

DETAILED DESCRIPTION INCLUSIVE OF PREFERRED EMBODIMENTS

In a composition of matter aspect the invention resides in 3-hydrazino-6-PY-pyridazine or pharmaceutically-acceptable acid-addition salt thereof, where PY is 4- or 3-pyridinyl or 4- or 3-pyridinyl having one or two lower-alkyl substituents. This compound is useful as a cardiotonic agent, as determined by standard pharmacological evaluation procedures. A preferred embodiment is 3-hydrazino-6-(4-pyridinyl)pyridazine or pharmaceutically-acceptable acid-addition salt thereof.

In a process aspect the invention resides in the process which comprises reacting 6-PY-3-pyridazinol with a chlorinating agent to produce 3-chloro-6-PY-pyridazine and reacting the 3-chloro compound with hydrazine to produce 3-hydrazino-6-PY-pyridazine, where PY is defined as above, a preferred embodiment being 4-pyridinyl for PY.

Another composition of matter aspect of the invention resides in 3-chloro-6-PY-pyridazine or pharmaceutically-acceptable acid-addition salt thereof, where PY is defined as above, a preferred embodiment being the product where PY is 4-pyridinyl.

A composition aspect of the invention resides in the cardiotonic composition for increasing cardiac contractility, said composition comprising a pharmaceutically-acceptable carrier and, as the active component thereof, the cardiotonic 3-hydrazino-6-PY-pyridazine or pharmaceutically-acceptable acid-addition salt thereof, a preferred embodiment being the compound where PY is 4-pyridinyl.

A method aspect of the invention resides in the method for increasing cardiac contractility in a patient requiring such treatment which comprises administering orally or parenterally in a solid or liquid dosage form to such patient an effective amount of the cardiotonic 3-hydrazino-6-PY-pyridazine or pharmaceutically-acceptable acid-addition salt thereof, a preferred embodiment utilizing the cardiotonic where PY is 4-pyridinyl.

The symbol PY as used here, e.g., as the 6-substituent in 3-hydrazino-6-PY-pyridazine, means 4- or 3-pyridinyl or 4- or 3-pyridinyl having one or two "lower-alkyl" substituents, illustrated by 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl, and the like.

The 3-hydrazino-6-PY-pyridazine and 3-chloro-6-PY-pyridazine are useful both in the free base form and in the form of acid-addition salts, and both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial cardiotonic properties inherent in the free base of 3-hydrazino-6-PY-pyridazine are not vitiated by side effects ascribable to the anions. In practicing the invention, it is convenient to use the free base form; however, appropriate pharmaceutically-acceptable salts within the scope of the invention are those derived from mineral acids such as hydrochloric acid, sulfuric acid, phosphoric acid and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid-addition salts of said basic compound are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said basic compound are preferred, all acid-addition salts are within the scope of the invention. All acid-addition salts are useful as sources of the free base form even if the particular salt per se is desired only as an intermediate product, as for example when the salt is formed only for purposes of purification or identification, or when it is used as an intermediate in preparing a pharmaceutically-acceptable salt by ion exchange procedures.

The molecular structures of 3-hydrazino-6-PY-pyridazine and 3-chloro-6-PY-pyridazine assigned on the basis of evidence provided by infrared, nuclear magnetic resonance and mass spectra, and by the correspondence of calculated and found values for the elementary analyses.

The manner of making and using the instant invention will now be generally described so as to enable a person skilled in the art of pharmaceutical chemistry to make and use the same, as follows.

The following examples will further illustrate the invention without, however, limiting it thereto.

The chlorination of 6-PY-3-pyridazinol (tautomeric with 6-PY-3(2H)-pyridazinone) to produce 3-chloro-6-PY-pyridazine is conveniently carried out by heating 6-PY-3-pyridazinol with a chlorinating agent, preferably phosphorus oxychloride on a steam bath. Alternatively, other chlorinating agents that can be used are phosphorus trichloride and phenylphosphonyl dichloride ($C_6H_5POCl_2$). The reaction can be run by heating the reactants at about 70° to 120° C., preferably about 90°–100° C., in the absence or presence of a suitable solvent e.g., dioxane, benzene, toluene, or the like. This chlorination is illustrated below in Examples D-1 through D-6.

The dehydrogenation of 4,5-dihydro-6-PY-3-pyridazinol (tautomeric with 4,5-dihydro-6-PY-3(2H)-pyridazinone) to produce 6-PY-3-pyridazinol is preferably carried out by reaction with bromine in hot acetic acid. The reaction is conveniently run at about 80°–120° C., preferably on a steam bath. This dehydrogenation is illustrated hereinbelow in Examples C-1 through C-6.

The preparation of the intermediate 4,5-dihydro-6-PY-3-pyridazinol is carried out by reacting 4-oxo-4-PY-butanenitrile with a hydrazine salt of a strong inorganic or organic sulfonic acid at about 65°–120° C. in a suitable solvent, preferably at about 80°–100° C. in a mixture of water and a lower-alkanol. The reaction is preferably run by refluxing 4-oxo-4-PY-butanenitrile with hydrazine sulfate in aqueous ethanol. Other hydrazine salts usable are hydrazine dihydrochloride, hydrazine dimethanesulfonate, and the like salts derived from phosphoric acid, ethanesulfonic acid, benzenesulfonic acid, and the like acids. Other loweralkanols useful as solvents are methanol, n-propanol, 2-propanol, n-butanol, 2-butanol and 2-methyl-n-propanol. This preparation is illustrated below in Examples B-1 through B-6.

The intermediate 4-oxo-4-butanenitriles are generally known compounds, e.g., Stetter et al., Chem. Ber. 107, 210 (1974), and are prepared by generally known methods. Preparation of these compounds is illustrated below in Examples A-1 through A-6.

The reaction of hydrazine with 3-chloro-6-(4-pyridinyl)pyridazine to produce 3-hydrazino-6-(4-pyridinyl)-pyridazine is carried out by heating the reactants at about 60° C. to 100° C. in a suitable solvent, preferably but optionally under an inert atmosphere. The reaction is preferably run at about 75° C. to 85° C. and is conveniently and preferably run by heating the reactants in refluxing isopropyl alcohol, preferably under nitrogen. Other suitable solvents include dioxane, ethanol, 2-methoxyethanol, or the like. Optionally, the reaction can be run in the absence of a solvent.

The following examples will further illustrate the invention without, however, limiting it thereto.

A. 4-Oxo-4-PY-butanenitriles

A-1. 4-Oxo-4-(4-pyridinyl)butanenitrile—To a stirred mixture containing 29.4 g. of sodium cyanide and 500 ml. of acetonitrile, after stirring said mixture for ten minutes, was added dropwise over a period of three hours a solution containing 64.2 g. of 4-pyridinecarboxaldehyde in 500 ml. of acetonitrile and the resulting mixture was stirred at room temperature for one hour. To the stirred mixture was added slowly over a period of one hour a solution of 24.5 g. of acrylonitrile in 200 ml. of acetonitrile and the resulting reaction mixture was stirred overnight at room temperature. The reaction mixture was stripped in vacuo of solvent at a temperature not exceeding 54° C. The semi-solid residue was cooled, mixed well with 400 ml. of chloroform, and the mixture filtered. The chloroform was distilled off in vacuo at a temperature not exceeding 50° C. and the residual oily reside extracted with three 200 ml. portions of toluene. The toluene solution was filtered through diatomaceous earth and the filtrate was distilled in vacuo below 50° C. to remove the toluene. The residue on chilling crystallized. A tiny sample was saved and the remainder was dissolved in 50 ml. of warm isopropyl alcohol. The solution was cooled and then diluted slowly with 125 ml. of ether, chilled and seeded with a crystal obtained from said tiny sample. The crystalline product that separated was collected, washed with 25 ml. of 1:3 (v:v) mixture of isopropyl alcohol:ether, and air dried to yield 52.1 g. of 4-oxo-4-(4-pyridinyl)butanenitrile, m.p. 53.5°–55° C.

Following the procedure described in Example A-1 but using in place of 4-pyridinecarboxaldehyde a molar equivalent quantity of the appropriate 4- or 3-PY-carboxaldehyde, it is contemplated that there can be obtained the corresponding 4-oxo-4-PY-butanenitriles of Examples A-2 thru A-6, respectively.

A-2. 4-Oxo-4-(3-pyridinyl)butanenitrile.
A-3. 4-(2-Methyl-3-pyridinyl)-4-oxobutanenitrile.
A-4. 4-(5-Methyl-3-pyridinyl)-4-oxobutanenitrile.
A-5. 4-(3-Ethyl-4-pyridinyl)-4-oxobutanenitrile.
A-6. 4-(2,6-Dimethyl-4-pyridinyl)-4-oxobutanenitrile.

B. 4,5-Dihydro-6-PY-3-pyridazinols

B-1. 4,5-Dihydro-6-(4-pyridinyl)-3-pyridazinol—A mixture containing 2.4 g. of 4-oxo-4-(4-pyridinyl)-butanenitrile (same as γ-oxo-γ-(4-pyridinyl)butyronitrile), 1.96 g. of hydrazine sulfate, 100 ml. of absolute ethanol and 100 ml. of water was refluxed with stirring overnight (about 15 hours). The reaction mixture was heated in vacuo to remove the solvent mixture. The remaining residue was taken up in water and filtered. The filtrate was neutralized with 10% aqueous sodium bicarbonate solution and a yellow solid separated. The solid was collected, washed with water, dried in vacuo over $P_2O_5$ for four hours. Its nuclear magnetic resonance (nmr) and mass spectra were found to be consistent with that of the desired product but showed traces of impurities. The solid was then recrystallized from absolute ethanol, dried in vacuo over $P_2O_5$ overnight to yield, as golden crystals, 0.9 g. of 4,5-dihydro-6-(4-pyridinyl)-3-pyridazinol, m.p. 185°–187° C., which is tautomeric with 4,5-dihydro-6-(4-pyridinyl)-3(2H)-pyridazinone.

The above reaction also can be run by using a molar equivalent quantity of hydrazine dihydrochloride or hydrazine di(methanesulfonate) in place of hydrazine sulfate.

Following the procedure described in Example B-1 but using in place of 4-oxo-4-(4-pyridinyl)butanenitrile a molar equivalent quantity of the corresponding 4-oxo-4-PY-butanenitrile, it is contemplated that there can be obtained the corresponding 6-PY-3-pyridazinols of Examples B-2 thru B-6.

B-2. 6-(3-Pyridinyl)-3-pyridazinol.
B-3. 6-(2-Methyl-3-pyridinyl)-3-pyridazinol.
B-4. 6-(5-Methyl-3-pyridinyl)-3-pyridazinol.
B-5. 6-(3-Ethyl-4-pyridinyl)-3-pyridazinol.
B-6. 6-(2,6-Dimethyl-4-pyridinyl)-3-pyridazinol.

C. 6-PY-3-pyridazinols

C-1. 6-(4-Pyridinyl)-3-pyridazinol—A 2 liter 3-necked round bottom flask was equipped with a mechanical stirrer, a reflux condenser and a dropping funnel. Into the flask was placed 750 ml. of acetic acid and 16.3 g. of 4,5-dihydro-6-(4-pyridinyl)-3-pyridazinol. The mixture was heated on a steam bath for about 20 minutes and then a solution containing 50 ml. of bromine and 150 ml. of acetic acid was initially added dropwise. The first 50 ml. of solution was added over a period of about 20 minutes whereupon solid began precipitating. The rest of the bromine solution was then added all at once followed by the addition of 60 ml. more of bromine. Most of the solid redissolved and the resulting mixture was heated with stirring on a steam bath for 6 hours and then allowed to stand at room temperature over the weekend (about 65 hours). A small amount of crystalline solid was filtered off and the filtrate was heated in vacuo to remove the solvent. The remaining residue was treated with 500 ml. of boiling water whereupon most of the residue dissolved. Sodium bisulfite was added to the hot mixture until bubbling of sulfur dioxide ceased. The mixture was made weakly basic to litmus paper by adding sodium bicarbonate. The solid that separated was collected, recrystallized from isopropyl alcohol and dried in a vacuum oven $P_2O_5$ at 45° C. for seventeen hours to produce 6.0 g. of 6-(4-pyridinyl)-3-pyridazinol hydrate (6:1), m.p. 222°–224° C., which is tautomeric with 6-(4-pyridinyl)-3(2H)-pyridazinone hydrate.

Following the procedure described in Example C-1 but using in place of 4,5-dihydro-6-(4-pyridinyl)-3-pyridazinol a molar equivalent quantity of the appropriate 4,5-dihydro-6-PY-3-pyridazinol, it is contemplated that there can be obtained the corresponding 6-PY-3-pyridazinols of Examples C-2 thru C-6.

C-2. 6-(3-Pyridinyl)-3-pyridazinol.
C-3. 6-(2-Methyl-3-pyridinyl)-3-pyridazinol.
C-4. 6-(5-Methyl-3-pyridinyl)-3-pyridazinol.
C-5. 6-(3-Ethyl-4-pyridinyl)-3-pyridazinol.
C-6. 6-(2,6-Dimethyl-4-pyridinyl)-3-pyridazinol.

D. 3-Chloro-6-PY-pyridazine

D-1. 3-Chloro-6-(4-pyridinyl)pyridazine—In a 50 ml. round bottom flask equipped with a magnetic stirrer, a reflux condenser and drying tube was placed a mixture of 2 g. of 3-(4-pyridinyl)-6-pyridazinol and 20 ml. of phosphorus oxychloride. The mixture was refluxed on a steam bath for 21 hours. The resulting solution was heated in vacuo to remove the excess phosphorus oxychloride and volatile reaction products and the resulting oily material was chilled in an ice bath and stirred with about 20 ml. of water. The resulting solution was filtered through diatomaceous earth and the filtrate was basified with sodium bicarbonate. The solid which separated was collected, recrystallized from absolute ethanol and dried in a vacuum oven over $P_2O_5$ for 17 hours to yield 1.6 g. of 3-chloro-6-(4-pyridinyl)pyridazine, m.p. 172°–173° C.

Acid-addition salts of 3-chloro-6-(4-pyridinyl)pyridazine are conveniently prepared by adding to a mixture of 0.5 g. of 3-chloro-6-(4-pyridinyl)pyridazine in about 10 ml. of aqueous methanol the appropriate acid, e.g. methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 3-chloro-6-(4-pyridinyl)pyridazine and the appropriate acid, e.g., lactic acid or hydrochloric acid, to prepare respectively the lactate or hydrochloride salt of 3-chloro-6-(4-pyridinyl)pyridazine in aqueous solution.

Following the procedure described in Example D-1 but using in place of 6-(4-pyridinyl)-3-pyridazinol a molar equivalent quantity of the appropriate 6-PY-3-pyridazinol, it is contemplated that there can be obtained the corresponding 3-chloro-6-PY-3-pyridazines of Examples D-2 thru D-6.

D-2. 3-Chloro-6-(3-pyridinyl)-3-pyridazine.
D-3. 3-Chloro-6-(2-methyl-3-pyridinyl)-3-pyridazine.
D-4. 3-Chloro-6-(5-methyl-3-pyridinyl)-3-pyridazine.
D-5. 3-Chloro-6-(3-ethyl-4-pyridinyl)-3-pyridazine.
D-6. 3-Chloro-6-(2,6-dimethyl-4-pyridinyl)-3-pyridazine.

E. 3-Hydrazino-6-PY-pyridazines

E-1. 3-Hydrazino-6-(4-pyridinyl)pyridazine—In a 250 ml. round bottom flask equipped with a reflux condenser an inlet tube and magnetic stirrer was placed a mixture containing 2.8 g. of 3-chloro-6-(4-pyridinyl)-pyridazine, 6 ml. of hydrazine and 75 ml. of isopropyl alcohol and the mixture was refluxed with stirring under an atmosphere of nitrogen for 4 hours. The solvent was dissolved off in vacuo and the residue was taken up with a minimum amount of water. The aqueous solution was basified with solid sodium bicarbonate whereupon a crystalline solid separated. The solid was recrystallized from water and dried in a vacuum oven over $P_2O_5$ at 40° C. overnight (about 15 hours) to yield 2.0 g. of 3-hydrazino-6-(4-pyridinyl)pyridazine, m.p. 178°–180° C.

Acid-addition salts of 3-hydrazino-6-(4-pyridinyl)-pyridazine are conveniently prepared by adding to a mixture of 1 g. of 3-hydrazino-6-(4-pyridinyl)pyridazine in about 20 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 3-hydrazino-6-(4-pyridinyl)pyridazine and the appropriate acid, e.g., lactic acid or hydrochloric acid, to prepare respectively the lactate or hydrochloride salt of 3-hydrazino-6-(4-pyridinyl)pyridazine in aqueous solution.

Following the procedure described in Example E-1 but using in place of 3-chloro-6-(4-pyridinyl)-3-pyridazine a molar equivalent quantity of the appropriate 3-chloro-6-PY-pyridazine, it is contemplated that there can be obtained the corresponding 3-hydrazino-6-PY-pyridazines of Examples E-2 thru E-6.

E-2. 3-Hydrazino-6-(3-pyridinyl)-pyridazine.
E-3. 3-Hydrazino-6-(2-methyl-3-pyridinyl)-pyridazine.
E-4. 3-Hydrazino-6-(5-methyl-3-pyridinyl)-pyridazine.
E-5. 3-Hydrazino-6-(3-ethyl-4-pyridinyl)-pyridazine.
E-6. 3-Hydrazino-6-(2,6-dimethyl-4-pyridinyl)-pyridazine.

The usefulness of 3-hydrazino-6-PY-pyridazine or salt as a cardiotonic agent is demonstrated by its effectiveness in standard pharmacological test procedures, for example, in causing a significant increase in the contractile force of the isolated cat atria and papillary muscle and in causing a significant increase in the cardiac contractile force in the anesthetized dog with low or minimal changes in heart rate and blood pressure. These known test procedures have been described, e.g., in U.S. Pat. No. 4,072,746, issued Feb. 7, 1978.

When tested by the isolated cat atria and papillary muscle procedure, 3-hydrazino-6-PY-pyridazine, when tested at a dose of 100 µg./ml., was found to cause significant increase, that is, greater than 25%, in papillary muscle force and a significant increase, that is, greater than 25%, in right atrial force, while causing only a low percentage increase (about one-third or less than the percentage increase in right atrial or papillary muscle force) in right atrial rate. For example, a preferred embodiment, 3-hydrazino-6-(4-pyridinyl)pyridazine, when tested by said cat atria and papillary muscle procedure at 100 µg./ml. was found to cause a papillary muscle force increase of 54% increase and a right atrial force increase of 38%.

When tested by said anesthetized dog procedure, 3-hydrazino-6-PY-pyridazine, when administered intravenously at 0.1, 0.3, 1.0 or 3.0 mg./kg. caused a significant increase, that is, greater than 25%, in cardiac contractile force or cardiac contractility with only one or minimal changes (less than 25%) in heart rate and blood pressure. For example, 3-hydrazino-6-(4-pyridinyl)-pyridazine when tested at said dose levels was found to cause cardiac contractile force increases ranging from about 33% to 142%.

The present invention includes within its scope a cardiotonic composition for increasing cardiac contractility, said composition comprising a pharmaceutically-acceptable carrier and, as the active component thereof, the cardiotonic 3-hydrazino-6-PY-pyridazine or pharmaceutically-acceptable acid-addition salt thereof. The invention also includes within its scope the method for increasing cardiac contractility in a patient requiring such treatment which comprises administering to such patient an effective amount of 3-hydrazino-6-PY-pyridazine or pharmaceutically-acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administrtion also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions may also contain adjuvants such as stabilising, preserving, wetting, emulsifying and dispersing agents.

They may be sterilized, for example by filtration through a bacteria-retaining filter, by incorporation of sterilising agents in the compositions, by irradiation or by heating. They may also be manufactured in the form of sterile solid compositions which can be dissolved in sterile water or some other sterile injectable medium immediately before use.

The percentages of active component in the said composition and method for increasing cardiac contractility may be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing the best judgement on the patient's behalf.

We claim:
1. 3-Chloro-6-PY-pyridazine or pharmaceutically-acceptable acid-addition salt thereof, where PY is 4- or 3-pyridinyl or 4- or 3-pyridinyl having one or two lower-alkyl substituents.
2. 3-Chloro-6-(4-pyridinyl)pyridazine.

UNITED STATES PATENT AND TRADEMARK OFFICE
CERTIFICATE OF CORRECTION

PATENT NO. : 4,354,026
DATED : October 12, 1982
INVENTOR(S) : G. Y. Lesher et al.

It is certified that error appears in the above-identified patent and that said Letters Patent are hereby corrected as shown below:

Column 1, line 56, delete "of".

Column 4, line 22, "4-butanenitriles" should read -- 4-PY-butanenitriles --.

Signed and Sealed this

Third Day of May 1983

[SEAL]

Attest:

Attesting Officer

GERALD J. MOSSINGHOFF

Commissioner of Patents and Trademarks